United States Patent
Lentz

(10) Patent No.: US 8,764,727 B2
(45) Date of Patent: Jul. 1, 2014

(54) REINFORCED RAPID EXCHANGE CATHETER

(75) Inventor: David Christian Lentz, Bloomington, IN (US)

(73) Assignee: Cook Medical Technologies LLC, Bloomington, IN (US)

(\*) Notice: Subject to any disclaimer, the term of this patent is extended or adjusted under 35 U.S.C. 154(b) by 172 days.

(21) Appl. No.: 13/254,117

(22) PCT Filed: Mar. 4, 2010

(86) PCT No.: PCT/US2010/026208
§ 371 (c)(1),
(2), (4) Date: Aug. 31, 2011

(87) PCT Pub. No.: WO2010/102105
PCT Pub. Date: Sep. 10, 2010

(65) Prior Publication Data
US 2012/0004606 A1    Jan. 5, 2012

Related U.S. Application Data

(60) Provisional application No. 61/158,047, filed on Mar. 6, 2009.

(51) Int. Cl.
| A61M 31/00 | (2006.01) |
| A61M 29/00 | (2006.01) |
| A61M 25/00 | (2006.01) |
| A61M 25/01 | (2006.01) |
| A61M 25/10 | (2013.01) |

(52) U.S. Cl.
CPC ..... A61M 25/005 (2013.01); *A61M 2025/0183* (2013.01); A61M 25/0053 (2013.01); *A61M 25/10* (2013.01)
USPC .................. 604/509; 604/103.09; 604/96.01

(58) Field of Classification Search
USPC .............. 604/509, 103.09, 103.1, 96.01, 524, 604/103.04, 527, 528, 529, 525; 606/194
See application file for complete search history.

(56) References Cited

U.S. PATENT DOCUMENTS

| 5,429,597 A | 7/1995 | DeMello et al. |
| 5,702,439 A | 12/1997 | Keith et al. |
| 2001/0044633 A1 | 11/2001 | Klint |
| 2005/0107821 A1 | 5/2005 | Shanley et al. |

FOREIGN PATENT DOCUMENTS

WO    WO 2008/005706    1/2008

OTHER PUBLICATIONS

International Search Report and Written Opinion for PCT/US2010/026208, dated Jun. 2, 2010.

*Primary Examiner* — Nicholas Lucchesi
*Assistant Examiner* — Brooke Matney
(74) *Attorney, Agent, or Firm* — Brinks Gilson & Lione

(57) ABSTRACT

A medical balloon catheter including a shaft comprised of a cross-wound coil tube and a sleeve surrounding the cross-wound coil tube. The cross-wound coil tube includes a monofilament inner coil disposed within a monofilament outer coil. The inner and outer coils are wound in opposite pitch directions. In at least one embodiment, at least one of the inner and outer coils includes a tapered distal section having a tapered diameter. In at least another embodiment, the inner coil extends distally beyond the distal end of the outer coil, providing increased flexibility in a distal portion of the shaft. An inflation balloon is attached to the distal end of the shaft. The shaft includes an inflation lumen formed through the inner coil and a wire guide lumen formed through the distal portion of the shaft and extending through the chamber of the balloon.

12 Claims, 5 Drawing Sheets

REINFORCED RAPID EXCHANGE CATHETER

CROSS-REFERENCE TO RELATED APPLICATIONS

This application is a national entry application under 35 U.S.C. §371 of, and claims priority under 35 U.S.C. §365(c) to, PCT Application Serial No. PCT/US2010/026208, filed Mar. 4, 2010, which claims priority to U.S. Provisional Patent Application Serial No. 61/158,047 filed, Mar. 6, 2009, each of which is hereby incorporated by reference herein in its entirety.

BACKGROUND OF THE INVENTION

1. Technical Field

The present application relates to medical catheters, and more specifically to medical catheters useful in endovascular and other body lumens.

2. Background

Medical catheters for use in endovascular or other body lumens typically require a variation in physical properties along different portions thereof. For example, a certain degree of stiffness is required for trackability and pushability near the proximal end while the distal end requires a great deal of flexibility. "Trackability" refers to the ability of the catheter to bend and advance effectively through the body lumen. "Pushability" involves the transmission of longitudinal forces along the catheter from its proximal end to its distal end so that a physician can push the catheter through the vascular or other lumenal system. A catheter having uniform properties throughout its length poses disadvantages in that it is likely to be too proximally flexible or too distally stiff. As a result, many catheter shafts are made from multiple materials along the shaft length, which poses problems of cost and efficiency in construction. Moreover, the junctions between the different materials may cause binding, kinking, or even separation and may require specialized connection means.

In view of the above, it is apparent that there exists a need for an improved medical balloon catheter.

BRIEF SUMMARY

It is sometimes desirable to exchange one catheter and/or balloon for another catheter (e.g., to "exchange out" a balloon catheter, and "exchange in" a stent-deployment catheter). The exchange is preferably executed by leaving the wire guide in place during removal of one catheter and using it as a guide for a second catheter. Short-wire catheters, in which the wire guide lumen does not extend the entire length of the catheter, are often easier to exchange than long-wire catheters, in which the wire guide lumen extends the entire length of the catheter.

The present invention provides a short-wire medical balloon catheter having a construction of a cross-wound coil tube. The embodiments described and claimed herein provide a catheter shaft having good pushability and trackability. The embodiments herein are adaptable for use in a variety of minimally invasive surgical treatments (including, e.g., angioplasty or bile duct dilation).

In one embodiment, the present invention provides a catheter comprising a shaft having a proximal end and a distal end. The shaft includes a cross-wound coil tube and a sleeve surrounding the cross-wound coil tube. The cross-wound coil tube includes an inner coil disposed within an outer coil, the inner and outer coils being wound in opposite pitch directions. The shaft includes a stiffer proximal portion and a more flexible distal portion. In this embodiment, the inner and outer coils extend from the proximal end in an overlapping arrangement defining the proximal portion and the inner coil extends distally beyond a distal end of the outer coil, defining the distal portion. The shaft includes an inflation lumen extending between the proximal and distal ends of the shaft and longitudinally through an interior of the inner coil.

The catheter further includes an inflation balloon extending from the distal end of the shaft. The balloon includes a proximal end and a distal end and a balloon wall interconnecting the proximal and distal ends. The proximal end of the balloon is fixed to the distal end of the shaft. The balloon wall defines a chamber in fluid communication with the inflation lumen. In this embodiment, a wire guide lumen is formed through the distal portion of the shaft and the balloon chamber.

In another embodiment, the present invention provides a catheter comprising a shaft having a proximal end and a distal end. The shaft includes a cross-wound coil tube and a sleeve surrounding the cross-wound coil tube. The cross-wound coil tube includes an inner coil disposed within an outer coil, the inner and outer coils being wound in opposite pitch directions. In this embodiment, at least one of the inner and outer coils includes a tapered distal section having a tapered diameter providing increased flexibility in a distal portion of the shaft. The shaft includes an inflation lumen extending between the proximal and distal ends of the shaft and longitudinally through an interior of the inner coil.

The catheter further includes an inflation balloon extending from the distal end of the shaft. The balloon includes a proximal end and a distal end and a balloon wall interconnecting the proximal and distal ends. The proximal end of the balloon is fixed to the distal end of the shaft. The balloon wall defines a chamber in fluid communication with the first lumen. In this embodiment, a wire guide lumen is formed through the distal portion of the shaft and the balloon chamber.

Further objects, features, and advantages of the present invention will become apparent from consideration of the following description and the appended claims when taken in connection with the accompanying drawings.

DETAILED DESCRIPTION OF THE INVENTION

The presently described embodiments of a cross-wound coil catheter shaft are adaptable for use in a variety of minimally invasive surgical applications (e.g. endoscopic procedures, angioplasty). The catheter device includes a balloon mounted at the distal end of a kink-resistant, cross-wound coil tube.

Figure 1:
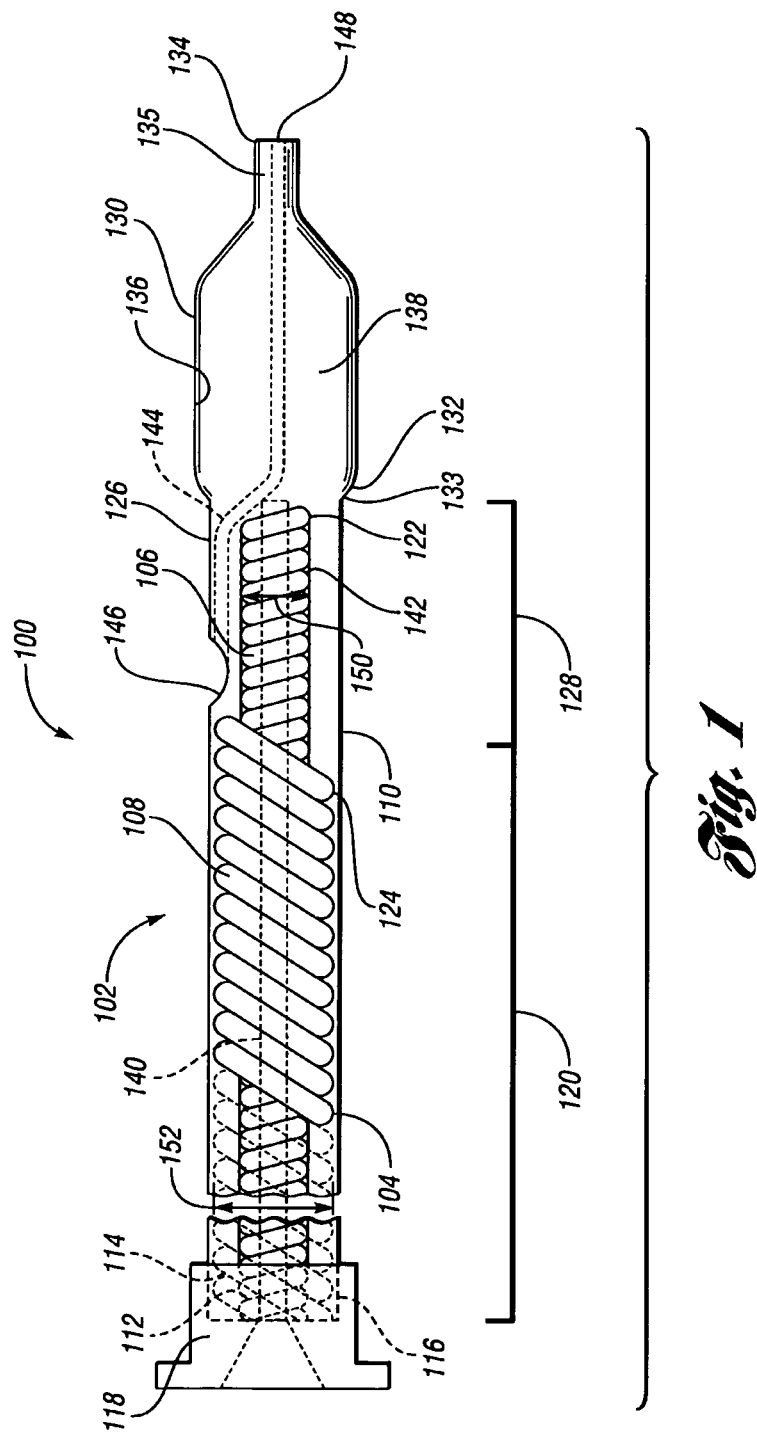
FIG. 1 is a side view of a catheter in accordance with one embodiment of the present invention.

FIG. 1 illustrates an embodiment of a catheter 100 with a shaft 102 constructed of a cross-wound coil tube 104. The cross-wound coil tube 104 includes two separate helically wound monofilament coils, including a smaller diameter inner coil 106 wound in one helical direction inserted into a larger diameter outer coil 108 wound in the opposite helical direction. In this embodiment, the inner and outer coils 106 and 108 are monofilament coils formed from a single filament tightly coiled about a longitudinal axis leaving a central lumen. Stainless steel is a typical material for fabricating the inner filament and the outer filament of the cross-wound coil tube 104. The inner and outer filaments of respective inner and outer coils 106 and 108 may be of, e.g., circular, oval, square, or rectangular cross-section. The inner and outer coils 106 and 108 are sized and fitted together so that the coils 106 and 108 are in intimate contact with one another.

The helical coil construction of the cross-wound coil tube 104 provides a highly flexible shaft 102 for the catheter 100, while the opposite pitch angles of the cross-wound inner and outer coils 106 and 108 act to lock the coils 106 and 108 against one another and to provide a high level of torque transmission during rotation of the cross-wound coil tube 104. The outer and inner diameters of the cross-wound coil tube 104 are selected to balance the requirements for strength, maneuverability, ease of passage through bodily lumens, and speed of balloon inflation and deflation. As with known catheters, the length of the cross-wound coil tube 104 of the shaft 102 is largely determined by the length of catheter required to perform the desired medical procedure.

Referring to FIG. 1, the shaft 102 is covered with a polymeric coating or sleeve 110. In this embodiment, the sleeve 110 has a constant outer diameter along the length of the shaft 102. Preferably, the sleeve 110 will generally have a diameter of between about 4 and 12 French. However, teachings of the present invention are also applicable to sleeves 110 of larger or smaller diameters and sleeves 110 which do not have a constant diameter along the length of the shaft.

In this embodiment, the sleeve 110 may comprise an extruded sleeve, shrink tube, extruded over-jacket, or dip coat. The sleeve 110 is preferably a thermoset material or a thermoplastic material and may comprise, for example, HDPE, PTFE, PEBA, PET, polyurethane, polyamide, polyolefin, nylon, or any combination thereof. For example, PET shrink tube has the advantage of providing an increased stiffness to a small diameter catheter shaft 102. On the other hand, a PEBA (Polyether Block Amide) shrink tube can be used with a larger diameter catheter shaft 102 where greater flexibility is desired. The type of sleeve 110 material may also be selected to complement other catheter components; for example, a nylon sleeve 110 may bond and interact better with a nylon expandable member such as a balloon or basket and/or a nylon wire guide lumen. Selection of coating materials, filament size, and diameter allow manipulation of the catheter shaft's 102 shore hardness to offer the desired functional properties.

As illustrated in FIG. 1, the proximal ends 112 and 114 of respective inner and outer coils 106 and 108 terminate at the proximal end 116 of the shaft 102 where the shaft 102 attaches to a hub 118. The inner and outer coils 106 and 108 extend distally from respective proximal ends 112 and 114 in an overlapping arrangement defining a stiffer proximal portion 120 of the shaft 102. In this embodiment, the distal end 122 of the inner coil 106 extends distally beyond the distal end 124 of the outer coil 108, defining a more flexible distal portion 128 of the shaft 102.

Thus, the outer diameter of the cross-wound coil tube 104 in the proximal portion 120 of the shaft 102 is defined by the outer diameter 152 of the larger diameter outer coil 108 and the outer diameter of the cross-wound coil tube 104 in the distal portion 128 of the shaft 102 is defined by the outer diameter 150 of the smaller diameter inner coil 106. As previously described with respect to this embodiment, the sleeve 110 has a constant diameter along the length of the shaft 102. As such, the region between the cross-wound coil tube 104 and the sleeve 110 surrounding the cross-wound coil tube 104 is greater in the distal portion 128 of the shaft 102 than in the proximal portion 120 of the shaft 102.

Preferably, the smaller diameter inner coil 106 extends distally from the larger diameter outer coil 108 a sufficient length so as to provide increased flexibility in the distal portion 128 of the shaft 102. In one example, the distal end 122 of the inner coil 106 may extend as little as about 2 cm from the distal end 124 of the outer coil 108, i.e., the length of the outer coil 108 may be as little as about 2 cm shorter than that of the inner coil 106. Alternatively, the distal end 122 of the inner coil 106 may extend past the distal end 124 of the outer coil 108 a distance equal to about the entire length of the outer coil 108, i.e., the length of the outer coil 108 may be about half the length of the inner coil 106.

As shown in FIG. 1, an inflation balloon 130 is fixed to the distal end 126 of the shaft 102. The balloon 130 includes a proximal neck 133 at its proximal end 132, a distal neck 135 at its distal end 134, and a balloon wall 136 interconnecting the proximal and distal ends 132 and 134 and defining a chamber 138. The proximal end 132 of the balloon 130 is attached to the distal end 126 of the shaft 102, for example, by a suitable adhesive, in any manner suitable for providing a fluid-tight seal. The balloon 130 may be any conventional balloon material and design used in such catheters, for example, the balloon 130 may be fabricated from polyethylene, terephthalate, or Nylon.

In this embodiment, the inner diameter of the inner coil 106 defines an inflation lumen 140 which longitudinally extends through the cross-wound coil tube 104 and opens into the balloon 130. The hub 118 at the proximal end 116 of the shaft 102 includes a port in fluid communication with the inflation lumen 140. Inflation media enters the inflation lumen 140 via the port formed through the hub 118 and the inflation lumen 140 supplies the inflation media to the balloon chamber 138. In other embodiments, the port may be located in other positions on the catheter 100.

Preferably, a coating 142 is provided on internal and/or external surfaces of at least a portion of the inner coil 106. The coating is selected to confer or improve one or more properties of reduced friction, flexibility, and sealing the inflation lumen 140 to prevent inflation media from escaping the inflation lumen 140. Sealing the inflation lumen 140 allows the inflation lumen 140 to be used, for example, for introduction of a medicative substance or radio-opaque contrast fluid. At least a portion of the outer coil 108 may include a similar coating on the internal and/or external surfaces and the sleeve 110 may subsequently be placed over the coating on the external surface of the outer coil 108. It is preferred that the entire catheter 100, including the sleeve 110, be impermeable to fluid inflation medium to prevent leakage of the fluid during the dilatation procedure.

If desired, the outer surface of the balloon 130 and the shaft 102, or any portion thereof, may be coated with a hydrophilic coating or other low-friction coating to minimize friction during positioning of the catheter 100.

As illustrated in FIG. 1, a wire guide lumen 144 is disposed within the distal portion 128 of the shaft 102 between the external surface of the inner coil 106 and the sleeve 110, i.e., in the region in which the outer coil 108 no longer overlaps the inner coil 106. A proximal port 146 is formed through the sleeve 110 of the shaft 102 proximal the distal end 126 of the shaft 102. Preferably, the proximal port 146 is formed through the sleeve 110 just distal the distal end 124 of the outer coil 108. A distal port 148 is formed through the distal end 134 of the balloon 130. In this embodiment, the wire guide lumen 144 is a tubular member extending between the proximal and distal ports 146 and 148. Preferably, the wire guide lumen 144 includes a first portion which extends distally from the proximal port 146 and runs parallel to the external surface of the inner coil 106 within the distal portion 128 of the shaft 102; a second portion which longitudinally traverses the balloon chamber 138 along a longitudinal axis of the balloon 130 and terminates at the distal port 148; and an intermediate portion connecting the first and second parallel portions. It is also within the scope of the present invention for the wire guide lumen 144 to extend distally from the proximal port 146 straight through the balloon chamber 138 before bending or curving to terminate at the distal port 148.

Preferably, the wire guide lumen 144 is bonded where the proximal end 132 of the balloon 130 meets the distal end 126 of the shaft 102, the wire guide lumen 144 entering the balloon chamber 138 through the proximal neck 133. In this embodiment, the wire guide lumen 144 extends through the balloon chamber 138 and is bonded within the distal neck 135 at the distal end 134 of the balloon 130. A wire guide can enter the proximal port 146, travel through the balloon 130 via the wire guide lumen 144, and exit through the distal port 148 of the wire guide lumen 144 at the distal end 134 of the balloon 130. The outer diameter of the proximal and distal ports 146 and 148 and the wire guide lumen 144 may be about 0.0035 inch, but may be sized to accommodate wire guides of various sizes. Forming a wire guide lumen 144 within the distal portion 128 of the shaft 102 confers the advantages of a short wire catheter in a single catheter 100.

Preferably, the wire guide lumen 144 is formed of a material having sufficient strength and thickness to prevent the wire guide lumen 144 from being compromised by potential high pressures of balloon inflation. Further, cross-lumen communication may be prevented. For example, the walls of the cross-wound coil tube 104 of the shaft 102 may be porous, and pressure exerted on an inflation fluid in the inflation lumen 140 may urge inflation fluid into the wire guide lumen 144. According to one aspect, this may be prevented by lining the tubular member of the wire guide lumen 144 with a liner such as, for example, PTFE, HDPE, and polyimide, although other materials may be used. Furthermore, an inner coating segment may be placed over the shaft 102 beneath the proximal port 146 of the wire guide lumen 144. The inner coating segment may be, for example, PEBA. These principles may be implemented in other embodiments of the invention as may be desirable due to fluid being passed through or injected into one of the lumens.

In the embodiment of FIG. 1, the outer diameter 152 of the outer coil 108 is approximately the same along its entire length. Similarly, the outer diameter 150 of the inner coil 106 is approximately the same along its entire length. The overlapping arrangement of the inner and outer coils 106 and 108 provides the cross-wound coil tube 104 with a larger outer diameter 152, and thus increased stiffness, in the proximal portion 120 of the shaft 102. In contrast, the non-overlapping arrangement of the inner and outer coils 106 and 108 provides the cross-wound coil tube 104 with a smaller outer diameter 150, and thus increased flexibility, in the distal portion 128 of the shaft 102.

Figure 2:
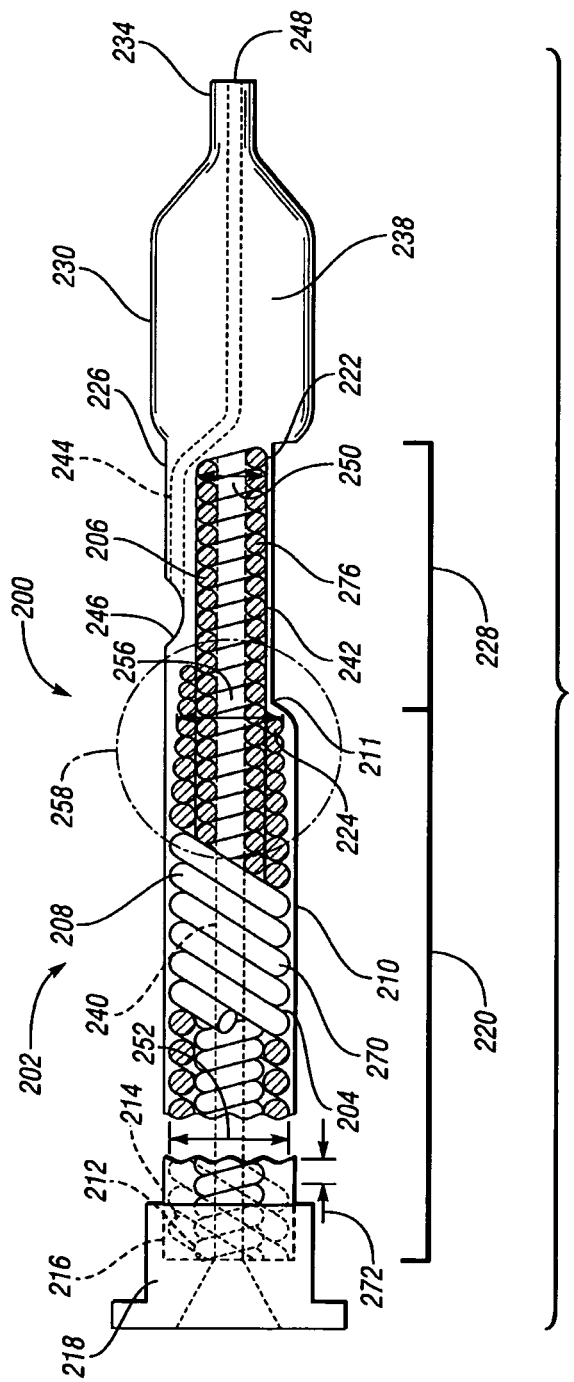
FIG. 2 is a side view, partly in cross-section, of a catheter in accordance with another embodiment of the present invention.

FIG. 2 illustrates another embodiment of a catheter 200 having a description similar to that in FIG. 1 and in which similar components are denoted by similar reference numerals increased by 100. The catheter 200 includes a shaft 202 constructed of a cross-wound coil tube 204 comprised of two separate helically wound monofilament coils, including a smaller diameter inner coil 206 wound in one helical direction disposed within a larger diameter outer coil 208 wound in the opposite helical direction in a similar manner to that described with respect to FIG. 1.

In this embodiment, the sleeve 210 has a larger diameter along a proximal portion 220 of the cross-wound coil tube 204 and a smaller diameter along a distal portion 228 of the cross-wound coil tube 204, forming a stepped portion 211 between the proximal and distal portions 220 and 228 along a side of the shaft 202.

In FIG. 2, an inflation balloon 230 is fixed to the distal end 226 of the shaft 202 and the inflation lumen 240 defined within the inner coil 206 supplies inflation media to the balloon chamber 238. A coating 242 may be provided on internal and/or external surfaces of at least a portion of the inner coil 206. The coating is selected to confer or improve one or more properties of reduced friction, flexibility, and sealing the inflation lumen 240 to prevent inflation media from escaping the inflation lumen 240. At least a portion of the outer coil 208 may similarly include such a coating on the internal and/or external surfaces.

As shown in FIG. 2, the proximal ends 212 and 214 of respective inner and outer coils 206 and 208 terminate at the proximal end 216 of the shaft 202 where the shaft 202 attaches to a hub 218. The inner and outer coils 206 and 208 extend distally in an overlapping arrangement defining a stiffer proximal portion 220 of the shaft 202. In this embodiment, the distal end 222 of the inner coil 206 extends distally beyond the distal end 224 of the outer coil 208, defining a more flexible distal portion 228 of the shaft 202. Preferably, the smaller diameter inner coil 206 extends distally from the larger diameter outer coil 208 a sufficient length so as to provide increased flexibility in the distal portion 228 of the shaft 202. The distal end 222 of the inner coil 206 may extend about 2 cm from the distal end 224 of the outer coil 208 or the distal end 222 may extend past the distal end 224 a distance equal to about the entire length of the outer coil 208.

Figure 2A:
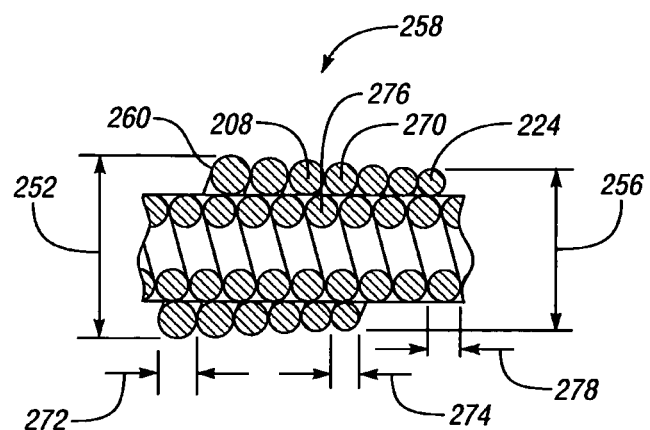
FIG. 2*a* is an enlarged view of the tapered distal portion of the outer coil in FIG. 2.
Figure 2B:
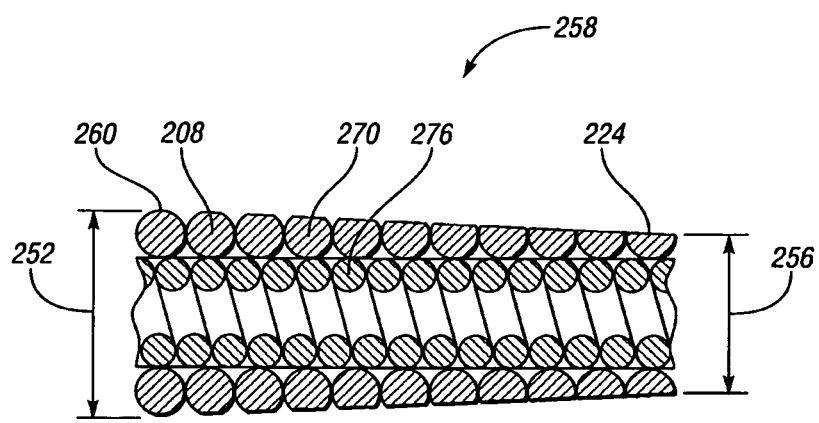
FIG. 2*b* is an enlarged view of a tapered distal portion of an outer coil of a catheter in accordance with another embodiment of the present invention.

In this embodiment, the outer diameter 252 at the proximal end 214 of the outer coil 208 is greater than the outer diameter 256 at the distal end 224 of the outer coil 208 to minimize the stiffness transition from the larger diameter out coil 208 to the smaller diameter inner coil 206 extending distally from the outer coil 208. As illustrated in FIGS. 2 and 2a-b, the outer coil 208 includes a tapered distal portion 258 wherein the outer diameter 252 at the proximal end 260 of the tapered distal portion 258 gradually or continuously decreases to the outer diameter 256 at the distal end 224 such that every successive point along the tapered distal portion 258 distal the proximal end 260 has a diameter successively smaller than the diameter 252 at the proximal end 260 and every successive point along the tapered distal portion 258 proximal the distal end 224 has a diameter successively larger than the diameter 256 at the distal end 224. Tapering the distal portion 258 of the outer coil 208 decreases the outer diameter of the outer coil 208 towards the distal end 224 of the outer coil 208, and thus decreases the outer diameter of the cross-wound coil tube 204. This increases flexibility towards the distal end 224 of the outer coil 208, and thus towards the distal end 226 of the shaft 202.

In this embodiment, the tapered distal portion 258 may be formed by initially tapering the distal portion of the wire or filament 270 which forms the outer coil 208 to define a gradually or continuously decreasing outer diameter along the distal portion of the filament 270. Thus, after coiling the filament 270 into the outer coil 208, the outer coil 208 has a natural decrease in the outer diameter of the tapered distal portion 258 as illustrated in FIGS. 2 and 2a. In this embodiment, forming the outer coil 208 from a pre-tapered filament 270 provides a continuous decline in the outer diameter of the tapered distal portion 258 as opposed to stepped or segmented regions of decreasing filament/coil outer diameter. This continuous decrease in outer diameter provides a continuous decrease in stiffness and thus minimizes the stiffness transition between the larger diameter outer coil 208 and the smaller diameter inner coil 206.

For example, the filament 270 which forms the outer coil 208 may have a larger outer diameter 272 of about 0.006 inch from the proximal end 214 to the proximal end 260 of the tapered distal portion 258. The filament 270 is tapered by any known means in the art to have a gradually decreasing outer diameter from the proximal end 260 of the tapered distal portion 258 to the distal end 224. Thus, at the distal end 224, the filament 270 defines a smaller outer diameter 274 of about 0.002 inch. In this embodiment, the wire or filament 276 which forms the inner coil 206 preferably has a constant outer diameter 278 of about 0.0035 inch.

In another embodiment, the tapered distal portion 258 of the outer coil 208 may be tapered via centerless grinding, electrolytic tapering, or any other technique suitable for providing a smooth, controlled, continuous decrease in diameter along the distal portion 258, as illustrated in FIG. 2b. In this embodiment, the outer coil 208 is formed from a wire or filament 270 having a constant outer diameter and the tapering occurs after the filament 270 is coiled into the outer coil 208. The tapered distal portion 258 provides a continuous decrease in stiffness and thus minimizes the stiffness transition between the larger diameter outer coil 208 and the smaller diameter inner coil 206. It is also within the scope of the present invention for the outer coil 208 to be tapered along its entire length, i.e., to have a gradually and continuously decreasing outer diameter from the proximal end 214 to the distal end 224, similar to the tapered distal portion 258 in FIGS. 2 and 2a-b. Alternatively, the inner diameter of the outer coil 208 may be tapered to increase the flexibility towards the distal end 224.

In FIG. 2, the outer diameter of the cross-wound coil tube 204 in the proximal portion 220 of the shaft 202 is defined by the outer diameter 252 of the larger diameter outer coil 208 and the outer diameter of the cross-wound coil tube 204 in the distal portion 228 of the shaft 202 is defined by the outer diameter 250 of the smaller diameter inner coil 206. As previously described with respect to this embodiment, the sleeve 210 has a stepped portion 211 between the proximal and distal portions 220 and 228 along a side of the shaft 202. However, along the other side of the shaft 202, the sleeve 210 extends linearly from the proximal end 216 to the distal end 226. Thus, the region between the cross-wound coil tube 204 and the sleeve 210 surrounding the cross-wound coil tube 204 is greater in the distal portion 228 of the shaft 202 than in the proximal portion 220 of the shaft 202 due to the decreasing diameter of the cross-wound coil tube 204 towards the distal end.

As illustrated in FIG. 2, a wire guide lumen 244 is disposed within the distal portion 228 of the shaft 202 between the external surface of the inner coil 206 and the sleeve 210, i.e., in the region in which the outer coil 208 no longer overlaps the inner coil 206. A proximal port 246 is formed through the sleeve 210 of the shaft 202 proximal the distal end 226 of the shaft 202. Preferably, the proximal port 246 is formed through the sleeve 210 just distal the distal end 224 of the outer coil 208. A distal port 248 is formed through the distal end 234 of the balloon 230. In this embodiment, the wire guide lumen 244 is a tubular member extending between the proximal and distal ports 246 and 248.

In this embodiment, the wire guide lumen 244 is formed within the catheter 200 and balloon 230 as described with respect to the wire guide lumen 144 of FIG. 1. Similarly, the wire guide lumen 244 is formed from a material having sufficient strength and thickness to prevent the wire guide lumen 244 from being compromised by potential high pressures of balloon inflation and to prevent cross-lumen communication. For example, the wire guide lumen 244 may include a liner formed from a material such as, for example, PTFE, HDPE, and polyimide, although other materials may be used. Furthermore, an inner coating segment may be placed over the shaft 202 beneath the proximal port 246 of the wire guide lumen 244. The inner coating segment may be, for example, PEBA. These principles may be implemented in other embodiments of the invention as may be desirable due to fluid being passed through or injected into one of the lumens.

Figure 3:
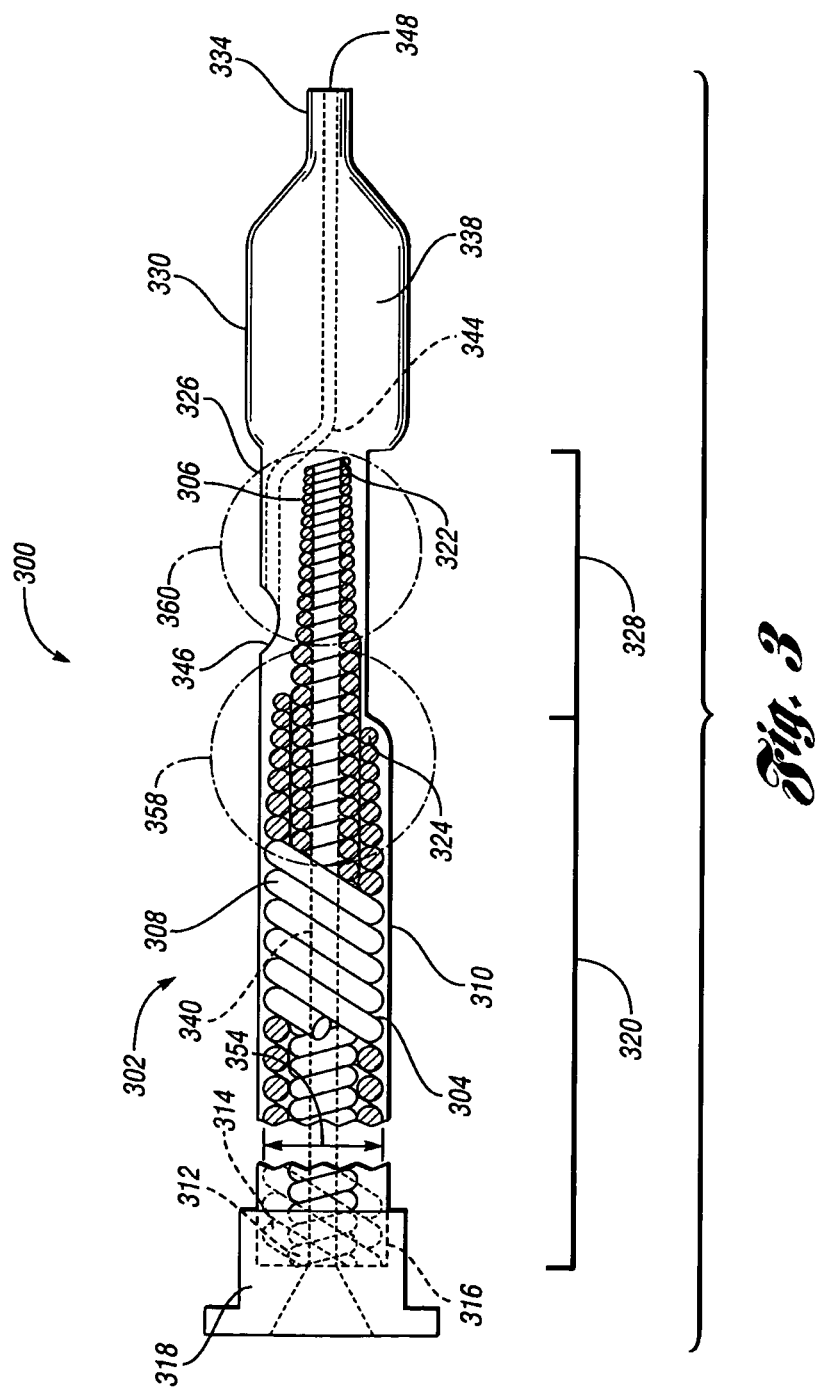
FIG. 3 is a side view, partly in cross-section, of a catheter in accordance with another embodiment of the present invention.

FIG. 3 illustrates another embodiment of a catheter 300 having a description similar to that in FIGS. 1 and 2 and in which similar components are denoted by similar reference numerals increased by 200 and 100, respectively. The catheter 300 includes a shaft 302 constructed of a cross-wound coil tube 304 comprised of two separate helically wound monofilament coils, including a smaller diameter inner coil 306 wound in one helical direction disposed within a larger diameter outer coil 308 wound in the opposite helical direction in a similar manner as that described with respect to FIGS. 1-2.

An inflation balloon 330 is fixed to the distal end 326 of the shaft 302. A hub 318 fixed to the proximal end 316 of the shaft 302 supplies inflation media to an inflation lumen 340 defined within the inner coil 306. The inflation media is delivered to the balloon chamber 338 via the inflation lumen 340.

As illustrated in FIG. 3, the proximal ends 312 and 314 of respective inner and outer coils 306 and 308 terminate at the proximal end 316 of the shaft 302. The inner and outer coils 306 and 308 extend distally in an overlapping arrangement defining a stiffer proximal portion 320 of the shaft 302. In this embodiment, the distal end 322 of the inner coil 306 extends distally beyond the distal end 324 of the outer coil 308, defining a more flexible distal portion 328 of the shaft 302 in which the outer coil 308 no longer overlaps the inner coil 306. Preferably, the smaller diameter inner coil 306 extends distally from the larger diameter outer coil 308 a sufficient length so as to provide increased flexibility in the distal portion 328 of the shaft 302. The distal end of 322 of the inner coil 306 may extend about 2 cm from the distal end 324 of the outer coil 308 or the distal end 322 may extend past the distal end 324 a distance equal to about the entire length of the outer coil 208.

In this embodiment, the inner and outer coils 306 and 308 include respective tapered distal portions 360 and 358 formed in accordance with the tapered distal portion 258 in any of the embodiments depicted in FIGS. 2a-b, or in any suitable manner known in the art. This minimizes the stiffness transition between the larger diameter outer coil 308 and the smaller diameter inner coil 306 and provides the shaft 302 with decreasing stiffness towards the distal end 326. Alternatively, the inner and outer coils 306 and 308 may be tapered along their entire lengths to provide an even smoother transition in stiffness along the length of the shaft 302. As illustrated, it is the outer diameter of the inner and outer coils 306 and 308 that is tapered. However, it is also within the scope of the present invention for the inner and outer coils 306 and 308 to have tapered inner diameters.

As illustrated in FIG. 3, a wire guide lumen 344 is disposed within the distal portion 328 of the shaft 302 between the external surface of the inner coil 306 and the sleeve 310, i.e., in the region in which the outer coil 308 no longer overlaps the inner coil 306. A proximal port 346 is formed through the sleeve 310 of the shaft 302 proximal the distal end 326 of the shaft 302. Preferably, the proximal port 346 is formed through the sleeve 310 just distal the distal end 324 of the outer coil 308. A distal port 348 is formed through the distal end 334 of the balloon 330. In this embodiment, the wire guide lumen 344 is a tubular member extending between the proximal and distal ports 346 and 348.

In this embodiment, the wire guide lumen 344 is formed within the catheter 300 and balloon 330 as described with respect to the wire guide lumen 144 of FIG. 1. Similarly, the wire guide lumen 344 is formed from a material having sufficient strength and thickness to prevent the wire guide lumen 344 from being compromised by potential high pressures of balloon inflation and to prevent cross-lumen communication. For example, the wire guide lumen 344 may include a liner formed from a material such as, for example, PTFE, HDPE, and polyimide, although other materials may be used. Furthermore, an inner coating segment may be placed over the shaft 302 beneath the proximal port 346 of the wire guide lumen 344. The inner coating segment may be, for example, PEBA. These principles may be implemented in other embodiments of the invention as may be desirable due to fluid being passed through or injected into one of the lumens.

Figure 4:
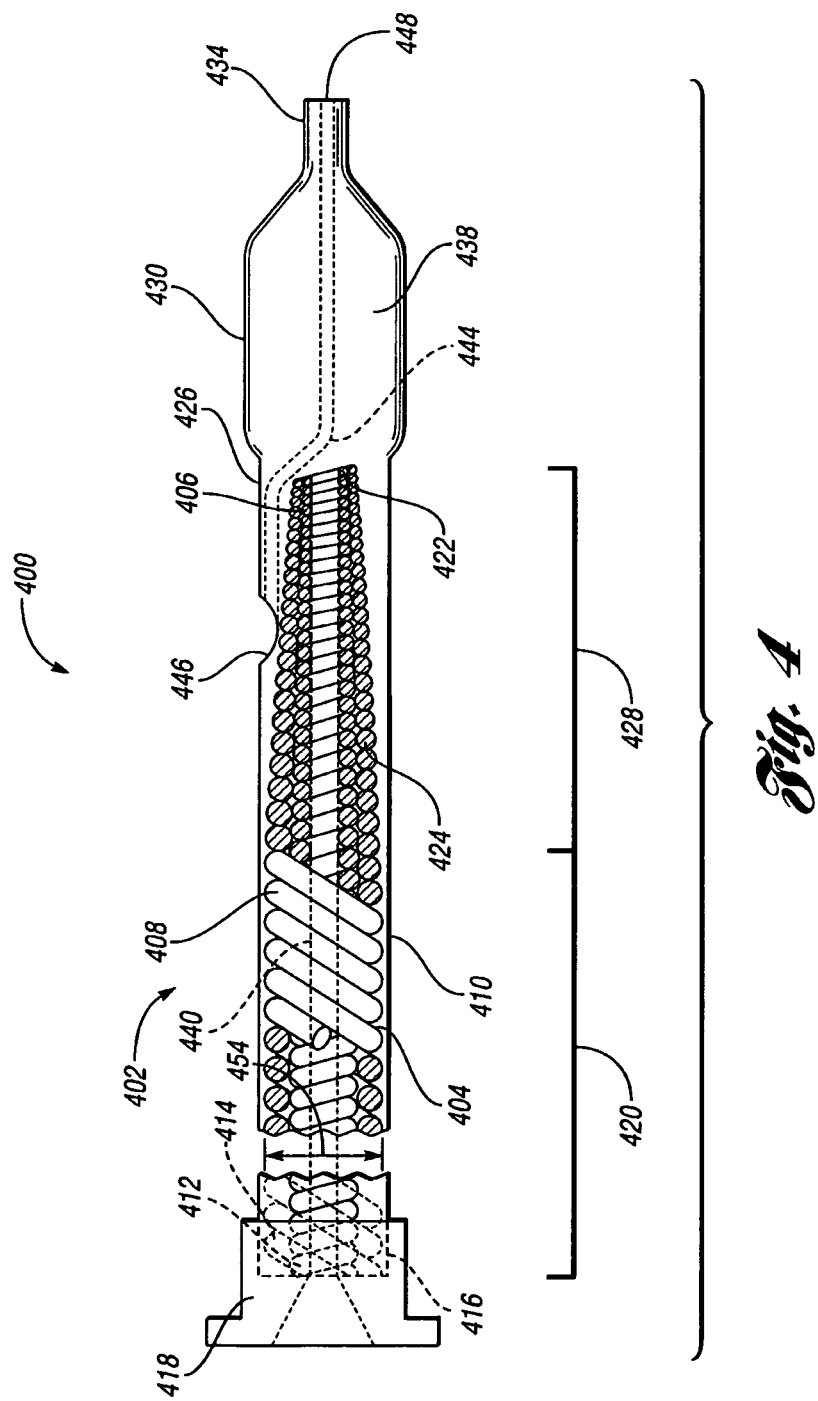
FIG. 4 is a side view, partly in cross-section, of a catheter in accordance with yet another embodiment of the present invention.

FIG. 4 illustrates another embodiment of a catheter 400 having a description similar to that in FIG. 3 and in which similar components are denoted by similar reference numerals increased by 100. The catheter 400 includes a shaft 402 constructed of a cross-wound coil tube 404 comprised of two separate helically wound monofilament coils, including a smaller diameter inner coil 406 wound in one helical direction disposed within a larger diameter outer coil 408 wound in the opposite helical direction in a similar manner as that described with respect to FIGS. 1-3.

An inflation balloon 430 is fixed to the distal end 426 of the shaft 402. A hub 418 fixed to the proximal end 416 of the shaft 402 supplies inflation media to an inflation lumen 440 defined within the inner coil 406. The inflation media is delivered to the balloon chamber 438 via the inflation lumen 440.

As illustrated in FIG. 4, the proximal ends 412 and 414 of respective inner and outer coils 406 and 408 terminate at the proximal end 416 of the shaft 402. In this embodiment, the inner and outer coils 406 and 408 extend distally in an overlapping arrangement from the proximal end 416 of the shaft 402 to the distal end 426 of the shaft 402. As illustrated in FIG. 4, both the inner and outer coils 406 and 408 are tapered distally in accordance with the tapered distal portion 258 in any of the embodiments depicted in FIGS. 2a-b, or in any suitable manner known in the art. The distally decreasing diameter of the inner and outer coils 406 and 408, and thus the cross-wound coil tube 404, provides increasing flexibility toward the distal end 426 of the shaft 402. The inner and outer coils 406 and 408 may be tapered along their entire lengths to provide an even smoother transition in stiffness along the entire length of the shaft 402. As illustrated, it is the outer diameter of the inner and outer coils 406 and 408 that is tapered. However, it is also within the scope of the present invention for the inner and outer coils 406 and 408 to have tapered inner diameters.

As illustrated in FIG. 4, the tapered inner coil 406 disposed within the tapered outer coil 408 provides the cross-wound coil tube 404 with a smaller outer diameter within the distal portion 428 of the shaft 402 and thus the region between the external surface of the outer coil 408 and the sleeve 410 is greater in the distal portion 428 than in the proximal portion 420. In this embodiment, a wire guide lumen 444 is disposed within this region, i.e., within the distal portion 428 of the shaft, between the external surface of the tapered outer coil 408 and the sleeve 410. A proximal port 446 is formed through the sleeve 410 of the shaft 401 proximal the distal end 426 of the shaft 402. A distal port 448 is formed through the distal end 434 of the balloon 430. In this embodiment, the wire guide lumen 444 is a tubular member extending between the proximal and distal ports 446 and 448. The wire guide lumen 444 is formed within the catheter 400 and the balloon 430 as described with respect to the wire guide lumen 144 of FIG. 1. Similarly, the wire guide lumen 444 may include a liner formed from any of the materials listed above with respect to FIGS. 1-3.

It is therefore intended that the foregoing detailed description be regarded as illustrative rather than limiting, and that it be understood that it is the following claims, including all equivalents, that are intended to define the spirit and scope of this invention.

I claim:

1. A medical balloon catheter comprising:
a shaft having a proximal end and a distal end and including a cross-wound coil tube and
a sleeve surrounding the cross-wound coil tube,
the cross-wound coil tube including an inner coil disposed within an outer coil, the inner and outer coils being wound in opposite pitch directions, the inner and outer coils extending from the proximal end in an overlapping arrangement defining a proximal portion of the shaft, the inner coil extending distally beyond a distal end of the outer coil and defining a distal portion of the shaft, the proximal portion having a greater stiffness than the distal portion,
wherein the inner coil extends beyond a distal end of the outer coil by a length that is between at least about 2 cm and a length equal to about an entire length of the outer coil, where the entire length of the outer coil is defined by a proximal end and the distal end of the outer coil,
the shaft including an inflation lumen extending between the proximal and distal ends of the shaft and longitudinally through an interior of the inner coil; and
a balloon having a proximal end and a distal end and a balloon wall interconnecting the proximal and distal ends, the proximal end fixed to the distal end of the shaft, the balloon wall defining a chamber in fluid communication with the inflation lumen,
wherein a wire guide lumen extends through the distal portion of the shaft and the balloon chamber; and
wherein the wire guide lumen comprises a tubular member extending from within the distal portion of the shaft and through the balloon chamber, the tubular member having a proximal tubular member end and a distal tubular member end, wherein the proximal tubular member end terminates at a proximal port just distal of the distal end of the outer coil and the distal tubular member end terminates near the distal end of the balloon.

2. The catheter of claim 1, further comprising a hub at the proximal end of the shaft for receiving inflation media and supplying the inflation media to the inflation lumen.

3. The catheter of claim 1, wherein each of the inner and outer coils is a monofilament coil.

4. The catheter of claim 1, wherein at least one of the inner and outer coils includes a tapered distal section having a tapered diameter.

5. The catheter of claim 4, wherein the outer coil is formed from a first filament and the inner coil is formed from a second filament, at least one of the first and second filaments including a tapered diameter along a distal section of the filament forming the tapered diameter along the tapered distal section of at least one of the inner and outer coils.

6. The catheter of claim 1, wherein the tubular member includes a liner formed of a material selected from the group consisting of HDPE, PTFE, and polyimide.

7. A medical balloon catheter comprising:
a shaft having a proximal end and a distal end and including a cross-wound coil tube and
a sleeve surrounding the cross-wound coil tube, the cross-wound coil tube including an inner coil disposed within an outer coil, the inner and outer coils being wound in opposite pitch directions, at least one of the inner and outer coils including a tapered distal section having a tapered diameter providing increased flexibility in a distal portion of the shaft,
wherein the inner coil is at least about 2 cm longer than and extends at least about 2 cm beyond a distal end of the outer coil, where a length of the outer coil is defined by a proximal end and the distal end of the outer coil,
the shaft including an inflation lumen extending between the proximal and distal ends of the shaft and longitudinally through an interior of the inner coil; and
a balloon having a proximal end and a distal end and a balloon wall interconnecting the proximal and distal ends, the proximal end fixed to the distal end of the shaft, the balloon wall defining a chamber in fluid communication with the inflation lumen, wherein a wire guide lumen extends through the distal portion of the shaft and the balloon chamber; and
wherein the wire guide lumen comprises a tubular member extending from within the distal portion of the shaft and through the balloon chamber, the tubular member having a proximal tubular member end and a distal tubular member end, wherein the proximal tubular member end terminates at a proximal port just distal of the distal end of the outer coil and the distal tubular member end terminates near the distal end of the balloon.

8. The catheter of claim 7, further comprising a hub at the proximal end of the shaft for receiving inflation media and supplying the inflation media to the inflation lumen.

9. The catheter of claim 7, wherein each of the inner and outer coils is a monofilament coil.

10. The catheter of claim 7, wherein the inner coil extends distally beyond a distal end of the outer coil by a length that is between at least about 2 cm and a length equal to about the entire length of the outer coil.

11. The catheter of claim 7, wherein the outer coil is formed from a first filament and the inner coil is formed from a second filament, at least one of the first and second filaments including a tapered diameter along a distal section of the filament forming the tapered distal section of at least one of the inner and outer coils.

12. The catheter of claim 7, wherein at least one of the inner and outer coils is tapered along substantially its entire length.

\* \* \* \* \*